United States Patent
Takahashi et al.

(10) Patent No.: US 6,444,841 B2
(45) Date of Patent: *Sep. 3, 2002

(54) HYDROQUINONE DIESTER DERIVATIVES AND THE METHOD FOR PRODUCING THE SAME

(75) Inventors: Ikuo Takahashi, Kobe; Hikaru Shibata, Himeji, both of (JP)

(73) Assignee: Daicel Chemical Industries, Ltd., Sakai (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/182,498

(22) Filed: Oct. 30, 1998

(51) Int. Cl.$^7$ .............................................. C07C 69/00
(52) U.S. Cl. ........................ 560/144; 560/76; 560/86; 560/146; 560/231; 560/109; 560/1; 560/130; 568/341; 568/763
(58) Field of Search ................................ 568/341, 763; 560/76, 79, 86, 146, 231, 130, 144, 109, 1

(56) References Cited

FOREIGN PATENT DOCUMENTS

| DE | 2149159 A | 4/1972 |
|---|---|---|
| EP | 0850910 A1 | 7/1998 |
| EP | 0850912 A1 | 7/1998 |
| JP | 477632 A | 4/1972 |

Primary Examiner—Paul J. Killos
Assistant Examiner—Taylor V. Oh
(74) Attorney, Agent, or Firm—Birch, Stewart, Kolasch & Birch, LLP

(57) ABSTRACT

A highly pure hydroquinone dietser derivative can be produced from the reaction product of ketoisophorone with an acylating agent in a high yield by a simple and easy operation. In the presence of an acid catalyst, a cyclohex-2-ene-1,4-dione derivative shown by the following formula (3) was allowed to react with an acylating agent (e.g., acetic anhydride), and the reaction product was purified by crystallization to obtain a hydroquinone diester derivative shown by the following formula (1). The compound (1) contains about 0 to 4% by weight of a catechol diester derivative represented by the following formula (2), being highly pure. As a solvent for crystallization, a mixed solvent of an organic carboxylic acid (e.g., acetic acid) corresponding to the acylating agent and water may be used.

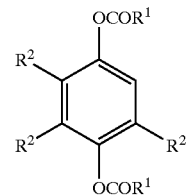

(1)

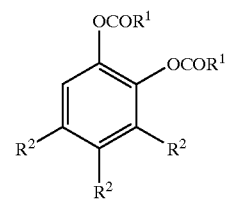

(2)

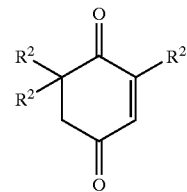

(3)

In the formulae, $R^1$ and $R^2$ each represents an alkyl group, a cycloalkyl group, an aryl group or a heterocyclic group.

6 Claims, No Drawings

HYDROQUINONE DIESTER DERIVATIVES AND THE METHOD FOR PRODUCING THE SAME

FIELD OF THE INVENTION

This invention relates to a hydroquinone diester derivative with high purity and the method for producing the same.

BACKGROUND OF THE INVENTION

A hydroquinone diester derivative (e.g., a trimethylhydroquinone diester, trimethylhydroquinone produced by hydrolyzing a trimethylhydroquinone diester) is useful as an intermediate of a medicine, and it is also one of the industrially important compounds as a raw material for vitamin E; an antioxidant for resins, higher fatty acids, higher alcohols, or fat and oils; and a polymerization inhibitor for polymerizable monomers.

Japanese Patent Application Laid-Open No. 7632/1972 (JP-A-47-7632) discloses a method for producing a trimethylhydroquinone diester by reacting 2,6,6-trimethylcyclohex-2-ene-1,4,-dione (ketoisophorone, KIP) with an acylating agent in the presence of an acid catalyst (e.g., a protonic acid catalyst or a Lewis acid catalyst).

In this method, however, a purified trimethylhydroquinone diester is obtained by, after neutralization and extraction, removing the acid catalyst from the reaction product by filtration, condensing the extract under reduced pressure, and recrystallizing the condensed extract with the use of hexane. Therefore, its purification process is complicated, and the yield is low. Moreover, when hexane is employed as a solvent for recrystallization, the purity of a trimethylhydroquinone diester can be improved only to a limited extent probably because the by-produces have poor solubility in hexane. Probably due to such reasons, in the reference mentioned above, the melting point of a trimethylhydroquinone dimethyl ester is disclosed to be in a wide range of 97 to 107° C. Moreover, since hexane has a low boiling point and the solubility in hexane of the object compound is considerably low, a large amount of hexane is required for recrystallization. Therefore, the purification process in this method is industrially disadvantageous.

SUMMARY OF THE INVENTION

It is, therefore, an object of the present invention to provide a hydroquinone diester derivative with high purity and a method for producing the same.

It is another object of the present invention to provide a method for producing a hydroquinone diester derivative with high purity in a high yield by simple operations.

A further object of the present invention is to provide a method for producing a hydroquinone diester derivative with high purity from the product formed by the esterification of 2,6,6-trimethylcyclohex-2-ene-1,4-dione (ketoisophorone, KIP) with an acylating agent and the transition reaction in a high yield by a simple operation.

The inventors of the present invention did intensive investigation, found that a trimethylhydroquinone diester with high purity can be obtained in a high yield by subjecting the reaction product of 2,6,6-trimethylcyclohex-2-ene-1,4-dione (KIP) with an acylating agent to a crystallization process, and achieved the present invention.

The hydroquinone diester derivative of the present invention is shown by the following formula (1):

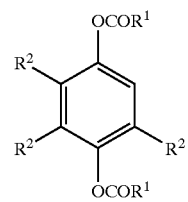

wherein $R^1$ represents an alkyl group, a cycloalkyl group, an aryl group or a heterocyclic group, and each $R^2$ is the same or different and represents an alkyl group, a cycloalkyl group, an aryl group, or a heterocyclic group, and comprises 0.001 to 2% by weight of a catechol diester derivative shown by the following formula (2):

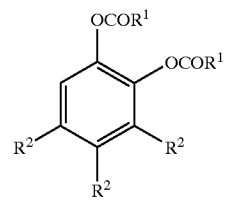

wherein $R^1$ and $R^2$ are the same as defined above.

In the method of the present invention, in the presence of a catalyst, a cyclohex-2-ene-1,4-dione derivative (e.g., 2,6,6-trisubstituted cyclohex-2-ene-1,4-dione) shown by the following formula (3):

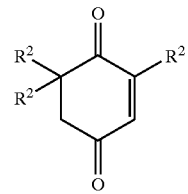

wherein $R^2$ has the same meaning mentioned above; is allowed to react with an acylating agent, and the reaction product is purified by crystallization to produce a hydroquinone diester derivative shown by the formula (1). The hydroquinone diester derivative (1) obtained in such manner contains about 0 to 2% by weight of a catechol diester derivative shown by the formula (2). The solvent for crystallization is usually a polar solvent, particularly a mixed solvent of an organic carboxylic acid corresponding to the above-mentioned acylating agent (in particular, acetic acid or the like), and water.

DETAILED DESCRIPTION OF THE INVENTION

As for $R^1$ and $R^2$ of the formulae (1) to (3), examples of an alkyl group include $C_{1-10}$ alkyl groups (e.g., $C_{1-8}$ alkyl groups such as methyl, ethyl, butyl, isobutyl, t-butyl, pentyl and hexyl). Examples of a cycloalkyl group include $C_{3-10}$ cycloalkyl groups (e.g., cyclohexyl group). Examples of an aryl group include $C_{6-12}$ aryl groups (e.g., phenyl group, substituted phenyl groups such as p-methylphenyl group). Examples of a heterocyclic group include aromatic or nonaromatic 5- or 6-membered heterocyclic groups having at least one heteroatom selected from the group consisting of nitrogen, oxygen and sulfur (e.g., furyl group, thienyl group, nicotinyl group and pyridyl group). In the compounds shown by the formulae (1) to (3), the species of the substituents $R^1$ and $R^2$ may be the same or different.

In the above hydroquinone diester derivative (1) and the catechol diester derivative (2), as a preferred $R^1$, there may be exemplified $C_{1-8}$ alkyl groups, particularly $C_{1-6}$ alkyl groups (e.g., $C_{1-4}$ alkyl groups such as methyl group and ethyl group). As a preferred $R^2$, there may be mentioned methyl group.

The features of the present invention reside in that a hydroquinone diester derivative (1) is highly pure, and that the content of a catechol diester derivative (2) produced as a by-product during the reaction is significantly low. Usually, the content of the catechol diester derivative (2) is substantially 2% by weight or less (i.e., an inevitable amount to 2% by weight). To be concrete, the content of the catechol diester derivative (2) as an impurity is about 0.001 to 2% by weight (e.g., about 0.001 to 1.5% by weight), preferably about 0.001 to 1% by weight, and more preferably about 0.001 to 0.8% by weight.

Such hydroquinone diester derivative (1) with high purity can be produced by reacting a cyclohex-2-ene-1,4-dione derivative shown by the formula (3) with an acylating agent in the presence of a catalyst and purifying the reaction product by crystallization. In this method, a hydroquinone diester derivative (1) containing substantially about 0% by weight (i.e., about 0 to 2% by weight) of the catechol diester derivative (2) can be also obtained.

As a compound shown by the formula (3), usually, there may be used 2,6,6-tri-$C_{1-4}$alkylcyclohex-2-ene-1,4-diones, particularly, 2,6,6-trimethylcyclohex-2-ene-1,4-dione (ketoisophorone, KIP).

As a catalyst, a protonic acid or a Lewis acid may be employed. As a protonic acid, there may be exemplified inorganic acids (e.g., sulfuric acid, hydrochloric acid, phosphoric acid, fluoroboric acid and hydrofluoric acid), organic acids (e.g., sulfonic acids such as p-toluenesulfonic acid, benzenesulfonic acid, methanesulfonic acid and ethanesulfonic acid; halocarboxylic acids or halogen-containing carboxylic acids such as chloroacetic acid, trichloroacetic acid and trifluoroacetic acid; and picric acid), and super strong acids with a Hammett's acidity function $H_0$ of smaller than −11.93 (e.g., $H_2SO_4$—$SO_3$, HF—$NbF_5$, HF—$TaF_5$, $SbF_5$, HF—$SbF_5$, $SbF_5$—$FSO_3H$, $FSO_3H$—$TaF_5$, $SbF_5$—$CF_3SO_3H$). As a Lewis acid, there may be exemplified $BF_3$, $BF_3OEt_2$, $AlCl_3$, $FeCl_3$, $ZnCl_2$, $TiCl_4$ and $SnCl_2$.

The amount of the catalyst may be an effective amount according to reaction conditions. For example, the amount may be about 0.001 to 100 parts by weight, preferably about 0.01 to 10 parts by weight, and more preferably about 0.1 to 5 parts by weight relative to 100 parts by weight of a substrate shown by the formula (3) (e.g., KIP).

The catalyst may be used as a solid catalyst (in particular, a solid acid catalyst). As a solid acid catalyst, there may be exemplified strong acidic ion-exchange resins (e.g., non-porous or porous ion-exchange resins containing a sulfonic acid group), super acidic ion-exchange resins (e.g., non-porous or porous ion-exchange resins having a very strong acid group such as —$CF_2CF_2SO_3H$), sulfates (e.g., $CaSO_4$, $Fe_2(SO_4)_3$, $CuSO_4$, $NiSO_4$, $AlSO_4$, $MnSO_4$, $BaSO_4$, $CoSO_4$, $ZnSO_4$, $(NH_4)_2SO_4$), metal oxides (e.g., $SiO_2$, $Al_2O_3$, $TiO_2$, $Fe_2O_3$, $ZrO_2$, $SnO_2$), compound oxides ($SiO_2$—$Al_2O_3$, $SiO_2$—$TiO_2$, $TiO_2$—$ZrO_2$, $SiO_2$—$ZrO_2$), zeolites (e.g., Y-type, X-type and A-type zeolites, ZSM-5 having an acidic OH group, mordenite, $VPI_5$, $AlPO_4$-5, $AlPO_4$-11), kaolin, and heteropolyacids (polyacids containing an element such as P, Mo, V, W, Si).

Among solid acid catalysts, as a strong acidic ion-exchange resin, there may be exemplified a styrene divinylbenzene sulfonic acid-series ion-exchange resin (produced by Organo, Ltd.; Amberlyst 15). As a super acidic ion-exchange resin, there may be exemplified a fluorinated sulfonic acid-series resin (produced by Aldrich Chemical Company, Inc., Naf ion NR 50; and produced by Du Pont, Nafion H).

The solid acid catalyst may be a solid catalyst in which a protonic acid (e.g., protonic acids such as the super strong acids mentioned above and strong acids) or a Lewis acid is supported on a carrier or a porous carrier.

As an acid to be supported (an acid catalyst), there may be exemplified the above-mentioned acid catalysts such as $SbF_5$, $TaF_5$, $BF_3$, $AlCl_3$, $AlBr_3$, $SbF_5$—HF, $SbF_5$—$FSO_3H$, $SbF_5$—$CF_3SO_3H$, $SO_4^{2-}$, and tungstic acid.

The carrier or supporter may be non-porous or porous. Examples of the carrier are metal oxides (e.g., $SiO_2$, $Al_2O_3$, $TiO_2$, $Fe_2O_3$, $ZrO_2$, $SnO_2$), compound oxides (e.g., $SiO_2$—$Al_2O_3$, $SiO_2$—$TiO_2$, $TiO_2$—$ZrO_2$, $SiO_2$—$ZrO_2$), zeolites, graphite, Pt-graphite, ion-exchange resins, metal sulfates, metal chlorides, metals (e.g., Pt, Au), alloys (e.g., Pt—Au, Ni—Mo, Al—Mg), polymers, salts (e.g., $SbF_3$, $AlF_3$), bauxite, activated carbon and charcoal. The surface area of a porous carrier (e.g., about 10 to 5,000 $m^2/g$), the pore volume and the average pore size are not particularly restricted. The amount of an acid component to be supported is, e.g., about 0.1 to 50% by weight, preferably about 1 to 25% by weight.

Concretely, there may be mentioned, e.g., $SbF_5/SiO_2$, $SbF_5/Al_2O_3$, $SbF_5/TiO_2$, $SbF_5/Fe_2O_3$, $SbF_5/ZrO_2$, $SbF_5/SnO_2$, SbF5/$SiO_2$—$Al_2O_3$, $SbF_5/SiO_2$—$TiO_2$, $SbF_5/TiO_2$—$ZrO_2$, $SbF_5/SiO_2$—$ZrO_2$, $AlCl_3/CuSO_4$, $SbF_5$—$HF/Al_2O_3$, $SbF_5$—$HF/SiO_2$—$Al_2O_3$, $SbF_5$—HF/activated carbon, $SbF_5$—$FSO_3H/Al_2O_3$, $SbF_5$—$FSO_3H/SiO_2$—$Al_2O_3$, $SbF_5$—$FSO_3H$/activated carbon, $SO_4^{2-}/ZrO_2$ (zirconyl sulfate), $SO_4^{2-}/TiO_2$ (titanyl sulfate), $SO_4^{2-}/Fe_2O_3$, $SO_4^{2-}/TiO_2$—$ZrO_2$, $WO_3/ZrO_2$ (zirconyl tungstate) and $Pt/SO_4^{2-}/ZrO_2$.

The amount of the solid acid catalyst may be an effective amount according to reaction conditions. For example, the amount is about 0.1 to 1,000 parts by weight, preferably about 1 to 100 parts by weight, and more preferably about 2 to 50 parts by weight (e.g., about 5 to 25 parts by weight) relative to 100 parts by weight of a substrate shown by the formula (3) (e.g., KIP).

The solid catalyst may be used as a dispersion (slurry) in the reaction system, and may be charged into a column in which reaction components can flow.

As an acylating agent, there may be used acylating agents having an aliphatic hydrocarbon group, an alicyclic hydrocarbon group, an aromatic hydrocarbon group or a heterocyclic group corresponding to $R^2$ of the formula (1). As an acylating agent, there may be used acid anhydrides, acyl halides and enol esters.

As an acid anhydride, there may be mentioned, e.g., anhydrides such as carboxylic anhydrides [e.g., straight- or branched chain $C_{1-10}$ alkyl-carboxylic acids ($C_{1-8}$alkyl-carboxylic acids such as acetic acid, propionic acid, butyric acid, isobutyric acid and valeric acid, particularly $C_{1-6}$alkyl-carboxylic acids], alicyclic carboxylic acids (e.g., $C_{3-10}$cycloalkyl-carboxylic acids such as cyclohexanecarboxylic acid), aromatic carboxylic acids (e.g., $C_{6-12}$aryl-carboxylic acids such as benzoic acid and toluic acid), halogen-containing carboxylic acids (e.g., chloroacetic acid, trichloroacetic acid and trifluoroacetic acid), and heterocyclic carboxylic acids (e.g., furancarboxylic acid, thiophenecarboxylic acid, nicotinic acid and pyridinecarboxylic acid). In particular, $C_{1-4}$alkyl-carboxylic anhydrides (e.g., $C_{2-4}$carboxylic anhydrides such as acetic anhydride and propionic anhydride) are preferred.

As an acyl halide, there may be mentioned acyl halides corresponding to the acid anhydrides mentioned above, e.g., $C_{1-10}$alkyl-carboxylic acid halides (e.g., $C_{1-8}$alkyl-carboxylic acid halides such as acetyl chloride, propionyl chloride and butyryl chloride), alicyclic carboxylic acid halides (e. g., cyclohexanecarboxylic acid halides), aromatic carboxylic acid halides (e.g., benzoic acid halides), and heterocyclic carboxylic acids (e.g., furancarboxylic acid halides). Among them, $C_{1-4}$alkylcarboxylic acid halides (e.g., $C_{2-4}$carboxylic acid halides such as acetyl chloride and propionyl chloride) are preferable.

As an enol ester, there may be exemplified isopropenyl acetate, isopropenyl propionate, isopropenyl isobutylate, isopropenyl butylate and cyclohexenyl benzoate.

The amount of such acylating agent is at least about two times mole (e.g., about 2 to 10 times mole), and preferably about 3 to 10 times mole relative to a substrate represented by the formula (3) (e.g., KIP). An excess acylating agent may be used as a solvent.

A 2,5,6-tri-substituted hydroquinone diester derivative (in particular, a 2,5,6-trimethylhydroquinone diester) represented by the formula (1) can be obtained, with a high conversion and a high selectivity, by reacting a compound shown by the formula (3)(particularly, 2,6,6-trimethylcyclohex-2-ene-1,4-dione) with an acylating agent.

Products represented by the formulae (1) and (2) correspond to an acylating agent to be used. For example, in the case where $R^2$ of the formula (3) represents methyl group, when acetic anhydride or acetyl chloride is employed, trimethylhydroquinone diacetate (1,4-diacethyloxy 2,3,5-trimethylbenzene) is produced as a trimethylhydroquinone diester shown by the formula (1). When using propionic anhydride, trimethylhydroquinone dipropionic acid ester (1,4-dipropionyl-2,3,5-trimethylbenzene) is formed. When using benzoic anhydride, trimethylhydroquinone dibenzoate (1,4-dibenzoyloxy-2,3,5-trimethylbenzene) is formed.

The reaction of the present invention may be conducted in the absence or presence of a solvent. As a solvent which is inert to the reaction, there may be mentioned, e.g., straight- or branched chain saturated or unsaturated hydrocarbon-series solvents (e.g., aliphatic hydrocarbons such as hexane, heptane and octane; alicyclic hydrocarbons such as cyclohexane; unsaturated aliphatic or alicyclic hydrocarbons such as octene and cyclohexene; aromatic hydrocarbons such as benzene, toluene and xylene), organic acid solvents (e.g., acetic acid, propionic acid, butyric acid, lactic acid, trichloroacetic acid and trifluoroacetic acid), ester-series solvents (e.g., methyl acetate, ethyl acetate and butyl acetate), halogen-containing solvents (e.g., methylene chloride, chloroform, carbon tetrachloride, 1,2-dichloroethane, chlorobenzene and dichlorobenzene), ether-series solvents (e.g., diethyl ether, diisopropyl ether, dibutyl ether, tetrahydrofuran, dioxane, ethylene glycol dimethyl ether and diethylene glycol dimethyl ether), ketone-series solvents (e.g., acetone, methyl ethyl ketone, methyl isobutyl ketone and diisobutyl ketone), non-protonic polar solvents [e.g., amide-series solvents (e.g., dimethyl-formamide and dimethylacetoaldehydeamide), amine-series solvents (e.g., N-methylpyrrolidone), sulfoxide-series solvents (e.g., dimethyl sulfoxide), nitrites (e.g., acetonitrile and benzonitrile), nitros (e.g., nitromethane, nitroethane and nitrobenzene)]. The solvent may be used singly or in a combination of two or more.

A small amount of the solvent is advantageous for increasing the efficiency of crystallization. The amount of the solvent is about 0 to 70% by weight, and preferably about 0 to 50% by weight relative to the reaction system.

In the reaction system of the present invention, the concentration of a 2,6,6-trisubstituted cyclohex-2-ene-1,4-dione (3) as a substrate is not particularly restricted, and may be, e.g., about 5 to 50% by weight (e.g., about 5 to 40% by weight), preferably about 10 to 45% by weight (e.g., about 10 to 35% by weight).

The reaction temperature may be selected from the range of about 0 to 150° C., preferably 10 to 120° C. (e.g., 10 to 100° C.). Usually, the reaction temperature is about 50 to 110° C. When the reaction temperature is too high, a hydroquinone diester derivative may be colored and the yield may tend to decrease. When the reaction temperature is too low, the reaction may tend to proceed at an extremely slow rate.

The reaction may be completed at a suitable stage, e.g., at the stage where the conversion of a compound shown by the formula (3) is 95% or more, particularly 98% or more.

In such reaction, a catechol diester derivative represented by the formula (2) is formed as a by-product, and this is what newly found. The amount of the by-product, the catechol diester derivative (2), varies according to the species of the catalyst used, its amount and the reaction conditions. For example, the amount of the catechol diester derivative (2) is about 1 to 50 mole % (in particular, about 4 to 15mole %). Moreover, the separation of the desired compound (1) from the compound (2) is difficult. Therefore, it is difficult to obtain a highly pure hydroquinone diester derivative (1) efficiently.

In the present invention, a solvent for crystallization is added to the reaction mixture, and crystallization is conducted to obtain the desired compound with high purity. Before being crystallized, the reaction mixture may be subjected to treatments such as neutralization with a base, filtration and condensation, if necessary. In order to obtain a hydroquinone diester derivative (1) with high purity by a simple purification operation, it is advantageous, if necessary, to neutralize the reaction mixture with a base, add a crystallization solvent, and lower the high temperature (e.g., a reaction temperature of about 50 to 120° C.) to the point where a crystal is separated out. Control over the temperature of the reaction mixture for crystallization can be done by, e.g., adding a crystallization solvent to a reactor and gradually lowering the temperature of the reactor to a temperature not higher than room temperature. The crystallization temperature may be selected from the range of, e.g., about −50° C. to 150° C., preferably about −10° C. to 100° C., and particularly about 0° C. to 80° C.

For neutralization of the reaction mixture, there may be used various bases, e.g., strong alkalis (e.g., alkaline metal hydroxides such as sodium hydroxide and potassium hydroxide) and weak alkalis (e.g., alkaline metal carbonates such as sodium hydrogencarbonate and potassium hydrogencarbonate, alikaline metal carbonates such as sodium carbonate). The amount of the base may be suitably selected from the range of about 0.5 to 10 equivalent relative to the amount of the acid catalyst. When using a solid catalyst as the catalyst, neutralization is not necessarily required, and the separated liquid (the reaction mixture from which the solid catalyst is separated by, e.g., filtration) may be subjected to the crystallization process.

As a solvent for crystallization, there may be used various polar solvents, e.g., water, alcohols (e.g., methanol and ethanol), esters (e.g., methyl acetate and ethyl acetate), ketones (e.g., acetone), ethers (e.g., dioxane, tetrahydrofuran and ethylene glycol dimethyl ether), non-protonic polar solvents (e.g., the above-mentioned amides), organic acids (e.g., acetic acid, propionic acid, butyric acid, lactic acid, trichloroacetic acid and trifluoroacetic acid), non-protonic polar solvents [amides (e.g., dimethylformamide and dimethylacetoaldehydeamide], amines (e.g., N-methylpyrrolidone), sulfoxides (e.g, dimethylsulfoxide), nitrites (e.g., acetonitrile)], and mixed solvents thereof.

Preferred crystallization solvents include hydrophilic solvents (particularly, water, water-miscible solvents, and mixed solvents thereof). In particular, it is preferable that crystallization is carried out by adding a solvent comprising at least one component selected from the group consisting of organic carboxylic acids and water (e.g., a solvent comprising only an organic carboxylic acid, a solvent comprising only water, and a mixed solvent comprising an organic carboxylic acid and water) to the reaction mixture. As an organic carboxylic acid, there may be mentioned carboxylic acids corresponding to the above-mentioned acylating agent, e.g., aliphatic carboxylic acids (e.g., acetic acid, propionic acid, butyric acid and isopropylcarboxylic acid), alicyclic carboxylic acids (e.g., cyclohexanecarboxylic acid), aromatic carboxylic acids (e.g., benzoic acid) and heterocyclic carboxylic acids. Preferred organic carboxylic acids are water-miscible carboxylic acids, particularly acetic acid.

When using an acid anhydride (e.g., acetic anhydride) as an acylating agent, an organic carboxylic acid (e.g., acetic acid) is formed by the reaction. When a suitable amount of an organic carboxylic acid (e.g., acetic acid) and water are added after the reaction is completed, the residual acid anhydride (e.g., acetic anhydride) can be converted into an organic carboxylic acid (e.g., acetic acid), and the solvent-system of the reaction mixture can be adjusted to a solvent composition suitable for crystallization (e.g., an aqueous solution of acetic acid). In the present specification, therefore, a solvent and a solvent composition constituting a crystallization solvent include a component produced by the reaction (e.g., acetic acid) and a component produced by the following treatments (e.g., acetic acid). In such manner, the reaction mixture does not need to be evaporated, and the further addition of a suitable crystallization solvent is not required. AS a result, the production process can be simplified.

When the crystallization solvent is a mixed solvent of a polar organic solvent (e.g., an organic carboxylic acid) and water, the proportion of a polar organic solvent (e.g., an organic carboxylic acid) to water may be selected from a wide range. For example, the former/latter=about 20/80 to 90/10 (weight ratio), preferably 30/70 to 80/20 (weight ratio), and more preferably about 40/60 to 70/30 (weight ratio). When the proportion of the polar organic solvent for crystallization (e.g., an organic carboxylic acid) is too small, the amount of the residue of the by-product increases. When the proportion of the polar organic solvent is too large, the yield of the desired compound decreases.

In the crystallization system, the concentration of a hydroquinone diester derivative (1) is usually about 5 to 40% by weight, and preferably about 10 to 35% by weight (e.g., about 15 to 35% by weight).

In the crystallization process, a seed crystal of a hydroquinone diester derivative (1) may be added. The amount of the seed crystal to be added may be selected from a wide range of, e.g., about 0.1 ppm to 10% by weight, preferably about 10 ppm to 5% by weight, and particularly about 100 ppm to 1% by weight relative to the mixture subjected to crystallization.

The crystallized product can be easily separated by, e.g., filtration. By washing and drying the crystallized product, the high-purity object compound (1) can be obtained. Water or an organic carboxylic acid aqueous solution of low concentration (e.g., acetic acid aqueous solution) can be used for washing the crystallized product.

According to the present invention, a highly pure hydroquinone diester derivative can be obtained efficiently. Particularly, crystallization, which is a simple and easy process, realizes the production of a highly pure hydroquinonediesterderivativeinahighyield. Moreover, a hydroquinone diester derivative with high purity can be produced from the reaction product of 2,6,6-trimethylcyclohex-2-ene-1,4-dione (KIP) with an acylating agent by a simple operation in a high yield.

EXAMPLES

The following examples are intended to describe the present invention in further detail and should by no means be interpreted as defining the scope of the invention.

Example 1

A three neck flask was charged with 10 g (0.066 mole) of 2,6,6-trimethylcyclohex-2-ene-1,4-dione (KIP), 20 g (0.196 mole) of acetic anhydride, and 0.25 g (2.5 mmole) of sulfuric acid, and the charged mixture was allowed to react at 60° C. for 5 hours. The analysis by gas chromatography after the completion of the reaction revealed the complete consumption of the starting material 2,6,6-trimethylcyclohexe-2-en-1,4-dione (KIP) (a conversion of 100%), and the formation of 2,5,6-trimethylhydroquinone diacetate (DAB) in a 92% yield and 3,4,5-trimethylcatechol diacetate (DAC) in a 6% yield. The reaction mixture was neutralized with 2.5 ml of an aqueous solution of 2N-sodium hydroxide.

Keeping the temperature of the mixture at 60° C., 13.4 g of acetic acid and 17.2 g of water (the solvent composition for crystallization: acetic acid/water=55/45 (weight ratio) are added. The temperature was gradually lowered from 60° C. to 15° C. to crystallize the object compound out. The crystallized product was filtrated, washed with water, and dried to give the object compound 2,5,6-trimethylhydroquinone diacetate (DAB).

yield: 76%; purity: 99.9% or more the content of the by-product DAC: 0.01% by weight (100 ppm); melting point: 109 to 110° C.

Example 2

A three neck flask was charged with 10 g (0.066 mole) of 2,6,6-trimethylcyclohex-2-ene-1,4-dione (KIP), 17 g (0.167 mole) of acetic anhydride, and 0.29 g (3 mmole) of sulfuric acid, and the charged mixture was allowed to react at 80° C. for 3 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinone diacetate (DAB) in a 91% yield and 3,4,5-trimethylcatechol diacetate (DAC) in a 5.8% yield.

The reaction mixture was neutralized with 3 ml of an aqueous solution of 2N-sodium hydroxide.

Keeping the temperature of the mixture at 80° C., 20.4 g of acetic acid and 21.9 g of water (the solvent composition for crystallization: acetic acid/water=55/45 (weight ratio) were added. Then, the temperature was gradually lowered from 80° C. to 10° C. to crystallize the object compound out. The crystallized product was filtrated, washed with water, and dried to give the object compound 2,5,6-trimethylhydroquinone diacetate (DAB)

yield: 74%; purity: 99.9% or more the content of the by-product DAC: 0.0015% by weight (15 ppm).

Example 3

A three neck flask was charged with 10 g (0.066 mole) of 2,6,6-trimethylcyclohex-2-ene-1,4-dione (KIP), 27 g(0.265 mole)of acetic anhydride, and 0.15 g(1.5 mmole) of sulfuric acid, and the charged mixture was allowed to react at 100° C. for 2 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinone diacetate (DAB) in a 90% yield and 3,4,5-trimethylcatechol diacetate (DAC) in a 7.5% yield. The reaction mixture was neutralized with 1.5 ml of an aqueous solution of 2N-sodium hydroxide.

Keeping the temperature of the mixture at 80° C., 1.9 g of acetic acid and 8.6 g of water (the solvent composition for crystallization: acetic acid/water=60/40 (weight ratio) were added. Then, the temperature was gradually lowered from 80° C. to 12° C. to crystallize the object compound out. The crystallized product was filtrated, washed with water, and dried to give the object compound 2,5,6-trimethylhydroquinone diacetate (DAB)

yield: 70%; purity: 99.9% or more the content of the by-product DAC: 0.025% by weight (250 ppm).

Example 4

A three neck flask was charged with 10 g (0.066 mole) of 2,6,6-trimethylcyclohex-2-ene-1,4-dione (KIP), 20 g (0.196 mole) of acetic anhydride, and 0.2 g (2 mmole) of sulfuric acid. Then, the charged mixture was allowed to react at 60° C. for 7 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinone diacetate (DAB) in a 91.8% yield and 3,4,5-trimethylcatechol diacetate (DAC) in a 5.3% yield. The reaction mixture was neutralized with 2.0 ml of an aqueous solution of 2N-sodium hydroxide.

Keeping the temperature of the mixture at 60° C., 12.5 g of acetic acid and 14.3 g of water (the solvent composition for crystallization: acetic acid/water=58/42 (weight ratio) were added. The temperature was gradually lowered from 60° C. to 14° C. to crystallize the object compound out. The crystallized product was filtrated, washed with water, and dried to give the object compound 2,5,6-trimethylhydroquinone diacetate (DAB)

yield: 81%; purity: 99.8% or more the content of the by-product DAC: 0.12% by weight (1,200 ppm).

Example 5

A three neck flask was charged with 10 g (0.066 mole) of 2,6,6-trimethylcyclohex-2-ene-1,4-dione (KIP), 30 g (0.294 mole) of acetic anhydride, 1.14 g (6 mmole) of p-toluenesulfonic acid, and 15.0 g of toluene as a solvent. Then, the charged mixture was allowed to react at 70° C. for 9 hours. The analysis by gas chromatography after the completion of the reaction revealed 94.0% conversion of the starting material 2,6,6-trimethylcyclohex-2-ene-1,4-dione (KIP), and the formation of 2,5,6-trimethylhydroquinone diacetate (DAB) in a 85% yield and 3,4,5-trimethylcatechol diacetate (DAC) in a 5.8% yield. The reaction mixture was neutralized with 10.0 ml of an aqueous solution of 2N-sodium hydroxide. The neutralized mixture was concentrated by an evaporator to distill the toluene off.

Keeping the temperature of the mixture at 70° C., 8.7 g of acetic acid and 32.4 g of water (the solvent composition for crystallization: acetic acid/water=50/50 (weight ratio) were added. The temperature was gradually lowered from 70° C. to 14° C. to crystallize the object compound out. The crystallized product was filtrated, washed with water, and dried to give the object compound 2,5,6-trimethylhydroquinone diacetate (DAB).

yield: 64%; purity: 99.2%; the content of the by-product DAC: 0.7% by weight.

Example 6

A three neck flask was charged with 10 g (0.066 mole) of 2,6,6-trimethylcyclohex-2-ene-1,4-dione (KIP), 27 g(0.265 mole) of acetic anhydride,and 0.06 g(0.2 mmole) of $SbF_5$/$FSO_3H$ as a catalyst. Then, the charged mixture was allowed to react at 70° C. for 3 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinone diacetate (DAB) in a 90% yield and 3,4,5-trimethylcatechol diacetate (DAC) in a 70% yield. The reaction mixture was neutralized with 0.4 ml of an aqueous solution of 2N-sodium hydroxide.

Keeping the temperature of the mixture at 70° C., 14.8 g of acetic acid and 20.6 g of water (a solvent composition for crystallization: acetic acid/water=55/45 (weight ratio) were added. The temperature was gradually lowered from 70° C. to 18° C. to crystallize the object compound out. The crystallized product was filtrated, washed with water, and dried to give the object compound 2,5,6-trimethylhydroquinone diacetate (DAB)

yield: 65%; purity: 99.5%; the content of the by-product DAC: 0.32% by weight.

Example 7

A three neck flask was charged with 10 g (0.066 mole) of 2,6,6-trimethylcyclohex-2-ene-1,4-dione (KIP), 27 g (0.265 mole) of acetic anhydride, and 0.79 g (4 mmole) of $BF_3OEt_2$ as a catalyst. Then, the charged mixture was allowed to react at 90° C. for 12 hours. The analysis by gas chromatography after the completion of the reaction revealed 99.5% conversion of the starting material 2,6,6-trimethylcyclohex-2-ene-1,4-dione (KIP), and the formation of 2,5,6-trimethylhydroquinone diacetate (DAB) in a 88.8% yield and 3,4,5-trimethylcatechol diacetate (DAC) in a 6.8% yield. The reaction mixture was neutralized with 4.0 ml of an aqueous solution of 2N-sodium hydroxide.

Keeping the temperature of the mixture at 70° C., 8.3 g of acetic acid and 19.9 g of water (the solvent composition for crystallization: acetic acid/water=54/46 (weight ratio) were added. The temperature was gradually lowered from 70° C. to 18° C. to crystallize the object compound out. The crystallized product was filtrated, washed with water, and dried to give the object compound 2,5,6-trimethylhydroquinone diacetate (DAB).

yield: 60%; purity: 99.7%; the content of the by-product DAC: 0.05% by weight.

Example 8

A three neck flask was charged with 10 g (0.066 mole) of 2,6,6-trimethylcyclohex-2-ene-1,4-dione (KIP), 30 g (0.294 mole) of acetic anhydride, and 1.33 g (10 mmole) of $AlCl_3$ as a catalyst. Then, the charged catalyst was allowed to react at 100° C. for 15 hours. The analysis by gas chromatography after the completion of the reaction revealed 94.0% conversion of the starting material 2,6,6-trimethylcyclohex-2-ene-1,4-dione (KIP), and the formation of 2,5,6-trimethylhydroquinone diacetate (DAB) in a 83.0% yield and 3,4,5-trimethylcatechol diacetate (DAC) in a 8.2% yield. The reaction mixture was neutralized with 10.0 ml of an aqueous solution of 2N-sodium hydroxide.

Keeping the temperature of the mixture at 80° C., 2.8 g of acetic acid and 24.8 g of water (the solvent composition for crystallization=acetic acid/water=52/48 (weight ratio) were added. The temperature was gradually lowered from 80° C. to 15° C. to crystallize the object compound out. The crystallized product was filtrated, washed with water, and dried to give the object compound 2,5,6-trimethylhydroquinone diacetate (DAB).

yield: 53%; purity: 99.8% or more the content of the by-product DAC: 0.089% by weight.

Example 9

A three neck flask was charged with 10 g (0.066 mole) of 2,6,6-trimethylcyclohex-2-ene-1,4-dione (KIP), 20 g(0.196 mole) of aceticanhydride, and 0.25 g(2.5 mmole) of sulfuric acid. Then, the charged mixture was allowed to react at 80° C. for 5 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinonediacetate (DAB) in a 93% yield and 3,4,5-trimethylcatechol diacetate (DAC) in a 5.0% yield. The reaction mixture was neutralized with 2.5 ml of an aqueous solution of 2N-sodium hydroxide.

Keeping the temperature of the mixture at 80° C., 12.4 g of acetic acid and 15.4 g of water (a solvent composition for crystallization: acetic acid/water=57/43 (weight ratio) were added. The temperature was gradually lowered from 80° C. to 18° C. to crystallize the object compound out. The crystallized product was filtrated, washed with water, and dried to give the object compound 2,5,6-trimethylhydroquinone diacetate (DAB).

yield: 82%; purity: 99.9% or more the content of the by-product DAC: 0.003% by weight.

Example 10

A three neck flask was charged with 10 g (0.066 mole) of 2,6,6-trimethylcyclohex-2-ene-1,4-dione (KIP), 20 g (0.196 mole) of acetic anhydride, and 0.2 g (2 mmole) of sulfuric acid. Then, the charged mixture was allowed to react at 60° C. for 8 hours. The analysis by gas chromatography after the completion of the reaction revealed the complete consumption of the starting material 2,6,6-trimethylcyclohex-2-ene-1,4-dione (KIP), and the formation of 2,5,6-trimethylhydroquinone diacetate (DAB) in a 91.8% yield and 3,4,5-trimethylcatechol diacetate (DAC) in a 5.3% yield. The reaction mixture was neutralized with 2.0 ml of an aqueous solution of 2N-sodium hydroxide.

Keeping the temperature of the mixture at 60° C., 15.4 g of acetic acid and 15.1 g of water (a solvent composition for crystallization: acetic acid/water=60/40 (weight ratio) were added. The temperature was gradually lowered from 60° C. to 14° C. to crystallize the object compound out. The crystallized product was filtrated, washed with water, and dried to give the object compound 2,5,6-trimethylhydroquinone diacetate (DAB).

yield: 68%; purity: 99.99% or more the content of the by-product DAC: not detected.

Comparative Example 1

A three neck flask was charged with 10 g (0.066 mole) of 2,6,6-trimethylcyclohex-2-ene-1,4-dione (KIP), 20 g (0.196 mole) of acetic anhydride, and 1.14 g (6 mmole) of p-toluenesulfonic acid as a catalyst. Then, the charged mixture was allowed to react at 80° C. for 9 hours. The analysis by gas chromatography after the completion of the reaction revealed 96% conversion of the starting material 2,6,6-trimethylcyclohex-2-ene-1,4-dione (KIP), and the formation of 2,5,6-trimethylhydroquinone diacetate (DAB) in a 85.1% yield and 3,4,5-grimethylcatechol diacetate (DAC) in a 7.1% yield. The reaction mixture was neutralized with 3.0 ml of an aqueous solution of 2N-sodium hydroxide, and 30 g of benzene and 30 g of water were added to extract the object compound. Then, the organic phase was concentrated by an evaporator. The amount of the obtained crude 2,5,6-trimethylhydroquinone diacetate (DAB) was 10.1 g (yield: 65%).

780 ml of hexane as a solvent for crystallization was added to the concentrate (crude DAB) and dissolved under reflux. Then, the mixture was cooled to 10° C. for recrystallization, filtrated, washedwithwater, anddried to obtain the object compound 2,5,6-trimethylhydroquinone diacetate (DAB). As shown below, the obtained DAB had a wide melting point range, and the melting point was depressed.

yield: 41%; purity: 96.3% or more the content of the by-product DAC: 2.9% by weight; melting point: 101 to 108° C.

What is claimed is:

1. A method for producing a hydroquinone diester derivative shown by the following formula (1) containing 0.001 to 1% by weight of a catechol diester derivative shown by the following formula (2):

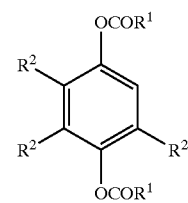

(1)

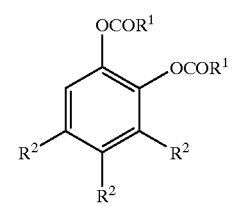

(2)

wherein $R^1$ represents an alkyl group, a cycloalkyl group, an aryl group or a heterocyclic group, and each $R^2$ is the same or different and represents an alkyl group, a cycloalkyl group, an aryl group, or a heterocyclic group, which method comprises
(a) reacting a cyclohex-2-ene-1,4-dione derivative shown by the following formula (3):

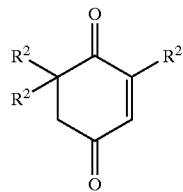

(3)

wherein $R^2$ is the same as defined above with an acylating agent in the presence of a catalyst at 50 to 120° C.,
(b) neutralizing the reaction mixture with a base,
(c) adding a polar solvent comprising water or a mixture of water and water-miscible organic carboxylic acids to the neutralized reaction mixture for adjusting the solvent-system of the mixture to a solvent composition suitable for crystallization of the compound represented by the formula (1), and
(d) lowering the temperature of the mixture to a temperature not higher than room temperature, without refluxing the mixture, to crystallize the reaction product of the formula (1), and wherein (c) the addition step and (d) the lowering-temperature step are respectively conducted as a single operation.

2. A method for producing a hydroquinone diester derivative according to claim 1, wherein the polar solvent for the crystallization comprises a mixed solvent of an organic carboxylic acid and water.

3. A method for producing a hydroquinone diester derivative according to claim 1, wherein the polar solvent for the crystallization comprises an aqueous solution of acetic acid.

4. A method for producing a hydroquinone diester derivative according to claim 1, wherein the polar solvent for the crystallization comprises a mixed solvent of an organic carboxylic acid and water with the proportion of the organic carboxylic acid to water=20/80 to 90/10 (weight ratio).

5. A method for producing a hydroquinone diester derivative according to claim 1, wherein said catalyst is a protonic acid catalyst or a Lewis acid catalyst.

6. A method for producing a hydroquinone diester derivative according to claim 1, wherein said acylating agent is a $C_{2-4}$ carboxylic anhydride or a $C_{2-4}$ carboxylic acid halide.

* * * * *

UNITED STATES PATENT AND TRADEMARK OFFICE
CERTIFICATE OF CORRECTION

PATENT NO. : 6,444,841 B2
DATED : September 3, 2002
INVENTOR(S) : Takahashi et al.

It is certified that error appears in the above-identified patent and that said Letters Patent is hereby corrected as shown below:

<u>Title page,</u>
Item [30], please insert the following missing Foreign Priority Data:

-- [30] Foreign Application Priority Data
November 12, 1997    (JP)    9-310199 --

Signed and Sealed this

Sixth Day of May, 2003

JAMES E. ROGAN
*Director of the United States Patent and Trademark Office*